(12) United States Patent
Sakhel

(10) Patent No.: US 8,403,842 B2
(45) Date of Patent: Mar. 26, 2013

(54) TRANSVAGINAL ULTRASOUND PROBE SPECULUM

(75) Inventor: Khaled Sakhel, Virginia Beach, VA (US)

(73) Assignee: Eastern Virgina Medical School, Norfolk, VA (US)

( * ) Notice: Subject to any disclaimer, the term of this patent is extended or adjusted under 35 U.S.C. 154(b) by 668 days.

(21) Appl. No.: 12/572,734

(22) Filed: Oct. 2, 2009

(65) Prior Publication Data

US 2011/0082375 A1  Apr. 7, 2011

(51) Int. Cl.
*A61B 1/32* (2006.01)

(52) U.S. Cl. ........ 600/221; 600/407; 600/437; 600/184; 600/201; 600/210; 600/219; 600/220

(58) Field of Classification Search .................. 600/407, 600/437, 439, 459, 220–221
See application file for complete search history.

(56) References Cited

U.S. PATENT DOCUMENTS

| | | | |
|---|---|---|---|
| 5,891,018 A * | 4/1999 | Wells | 600/226 |
| 6,210,330 B1 | 4/2001 | Tepper | |
| 6,432,048 B1 | 8/2002 | Francois | |
| 6,712,761 B2 | 3/2004 | Borodulin | |
| 6,960,166 B1 | 11/2005 | Wong et al. | |
| 2006/0224043 A1* | 10/2006 | Guinan | 600/220 |
| 2006/0276693 A1* | 12/2006 | Pacey | 600/188 |
| 2007/0135687 A1 | 6/2007 | Balas | |
| 2008/0312508 A1 | 12/2008 | Shulman | |

OTHER PUBLICATIONS

PCT/US10/051311 International Search Report (mailed Dec. 3, 2010) (2 pages).

* cited by examiner

*Primary Examiner* — James Kish
(74) *Attorney, Agent, or Firm* — Wilmer Cutler Pickering Hale and Dorr LLP

(57) ABSTRACT

A transvaginal ultrasound probe speculum is designed for use with a generally cylindrical elongated ultrasound probe. The speculum has an elongated blade having a proximal end and a distal end, and a connector, such as a collar. The speculum has a lever that cooperates with the collar and the elongated blade for pivoting the blade relative to the ultrasound probe so that the blade and the ultrasound probe serve as the blades of the speculum.

18 Claims, 5 Drawing Sheets

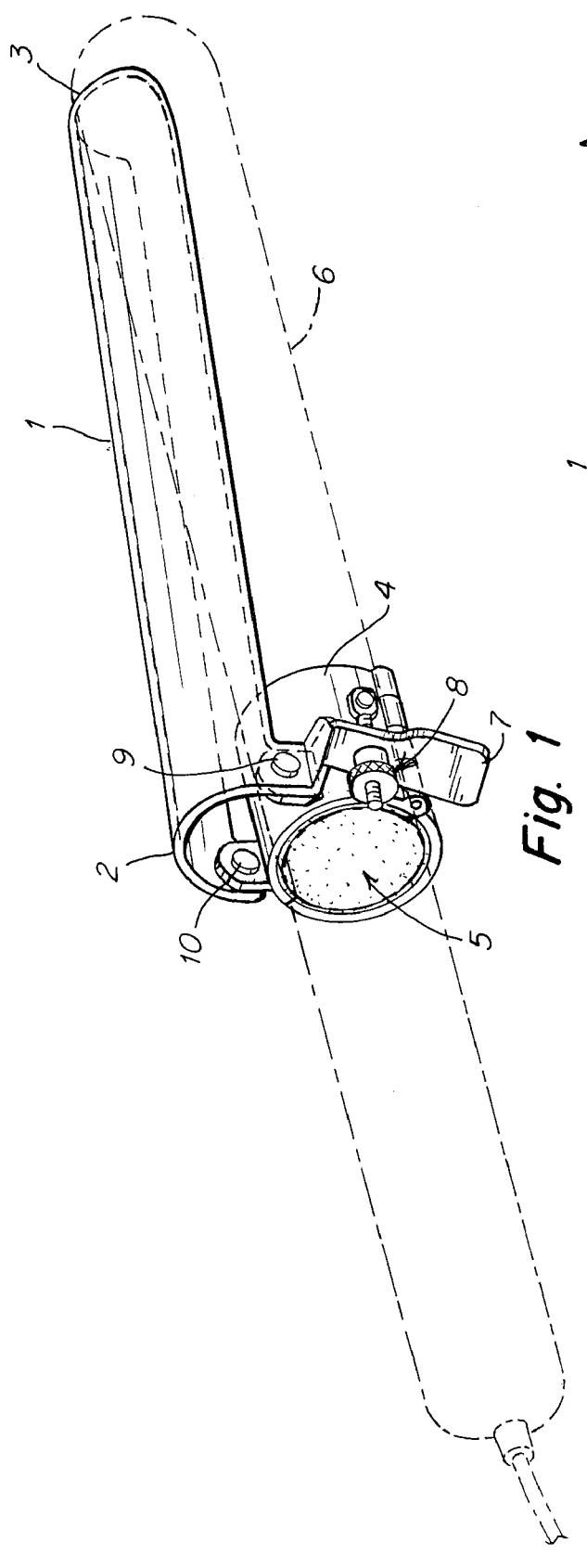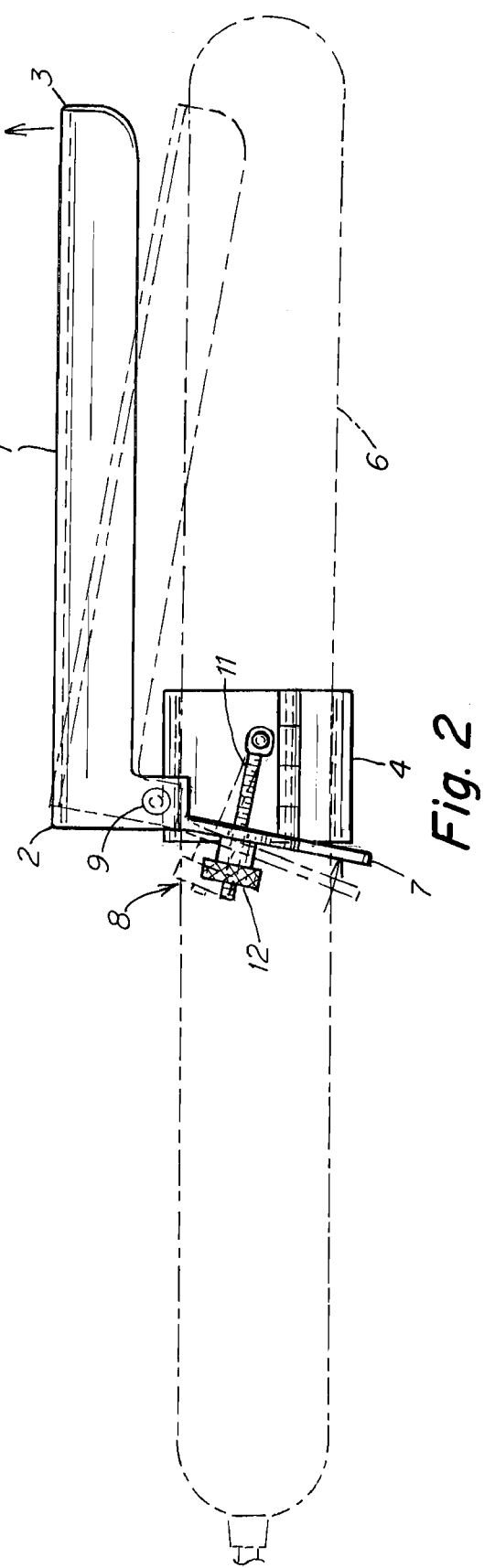

TRANSVAGINAL ULTRASOUND PROBE SPECULUM

FIELD

This disclosure relates to a transvaginal speculum with an ultrasound probe.

BACKGROUND

A significant number of transcervical procedures are performed annually worldwide, including in vitro fertilization (IVF), endometrial biopsies, insertion or removal of intrauterine devices (IUDs), and saline infusion sonography. Currently, many transcervical procedures are performed without visualization of the cervix or are performed with abdominal ultrasound guidance. Transabdominal ultrasound guidance can provide inadequate visualization of the cervical canal and uterine cavity. The visualization can be poor due to the position of the bowel between the skin and the uterus, and can be worsened if the patient is obese, or has a deep retroverted and retroflexed positioning of the uterus. Transabdominal ultrasound guidance also often requires a full, uncomfortable bladder for optimal visualization of the cervical canal and uterine cavity. This approach can require two people: one person to hold the abdominal ultrasound probe in the best orientation for cervical canal and uterine cavity visualization, and another to perform the procedure.

SUMMARY

A transvaginal speculum for use with a generally cylindrical elongated ultrasound probe and methods of using the transvaginal ultrasound probe speculum are described. The speculum has an elongated blade with a proximal end and a distal end, and is sized and shaped to form the blade of a vaginal speculum. For connecting to a generally cylindrical object, the speculum has a connector, such as a collar, that surrounds the probe and has a pivotal connection to pivotally cooperate with the proximal end of the elongated blade. The speculum has a lever that cooperates with the collar and the elongated blade for pivoting the blade relative to the ultrasound probe so that the blade and the ultrasound probe serve as the blades of the speculum.

In another aspect, the speculum includes an elongated blade having a proximal end and a distal end, and is sized and shaped to form the blade of a vaginal speculum. The speculum includes a generally cylindrical ultrasound probe having a proximal end and a distal end and having at least one transducer proximate to the distal end. The speculum can have a connector such as a collar that holds the probe and also cooperates pivotally with the proximal end of the blade. The speculum can have a lever that cooperates with the collar and the blade for pivoting the distal end of the blade relative to the ultrasound probe so that the blade and the ultrasound probe serve as the blades of the speculum. The speculum blades can consist essentially of the one blade and the ultrasound probe.

A method of performing a gynecological procedure on a patient is also described. A speculum is inserted into the patient's vagina. The speculum has an elongated blade and an ultrasound probe having a proximal end and a distal end and having at least one transducer proximate to the distal end. The ultrasound probe is used to provide images suitable to ultrasound viewing equipment.

The device allows a practitioner of gynecological procedures to have direct transvaginal ultrasound visualization to more easily and accurately guide catheters and instruments into the cervical canal and uterine cavity.

BRIEF DESCRIPTION OF THE FIGURES

FIG. 1 is a perspective view of an embodiment of a speculum in a closed position, and with an ultrasound probe in phantom.

FIG. 2 is a side view of the speculum of FIG. 1 in an open position, and with an ultrasound probe in phantom.

DETAILED DESCRIPTION

Figure 3:
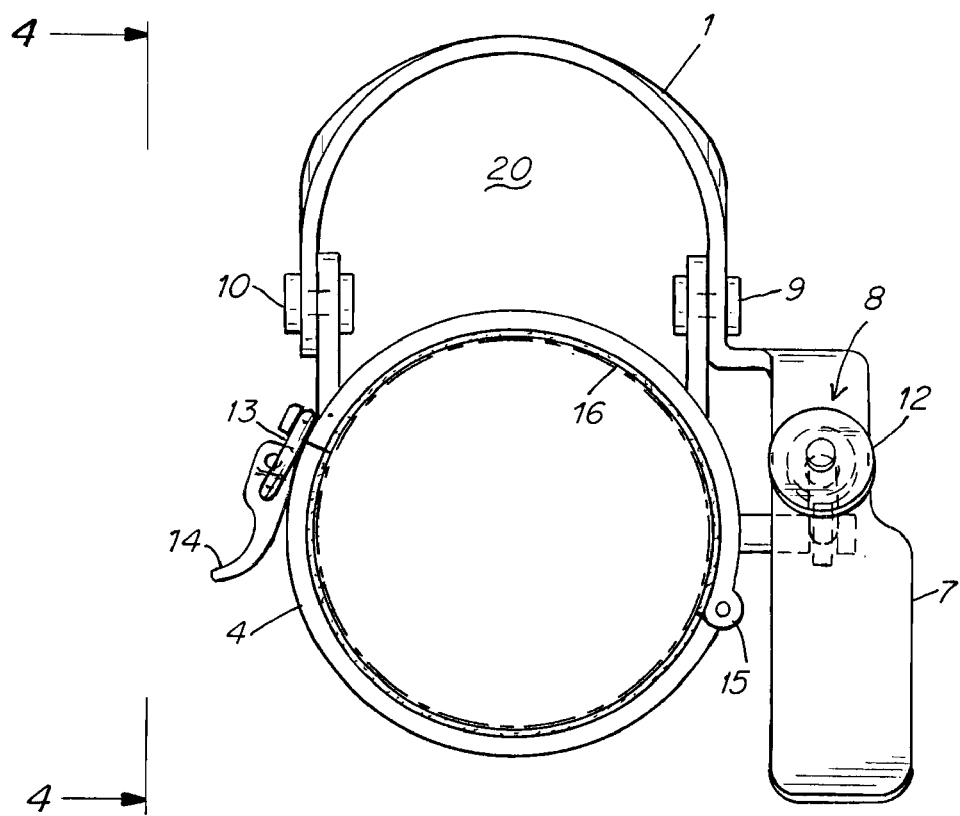
FIG. 3 is an end view of the speculum.

Referring to FIGS. 1 and 2, a transvaginal speculum has an elongated blade 1 having a proximal end 2 and a distal end 3, and is sized and shaped to form the blade of a vaginal speculum for humans. Elongated blade 1 can have any length suitable for the speculum function, e.g., from about 6 inches (15 cm) to about 8 inches (20 cm). Blade 1 can include plastic or metal.

The other blade of the speculum is formed by a generally cylindrical ultrasound probe 6 (shown in FIGS. 1 and 2 in phantom). The speculum has a connector for connecting blade 1 to probe 6 that allows connection and pivotable movement. In one embodiment, the connector includes collar 4 for surrounding and clamping probe 6. Collar 4 also has components for pivotally cooperating through pivots 9, 10 at proximal end 2 of blade 1, and has an opening 5 for receiving and holding ultrasound probe 6. When probe 6 is held in the collar, the pivoting action pivots the blade 1 relative to probe 6.

Figure 6:
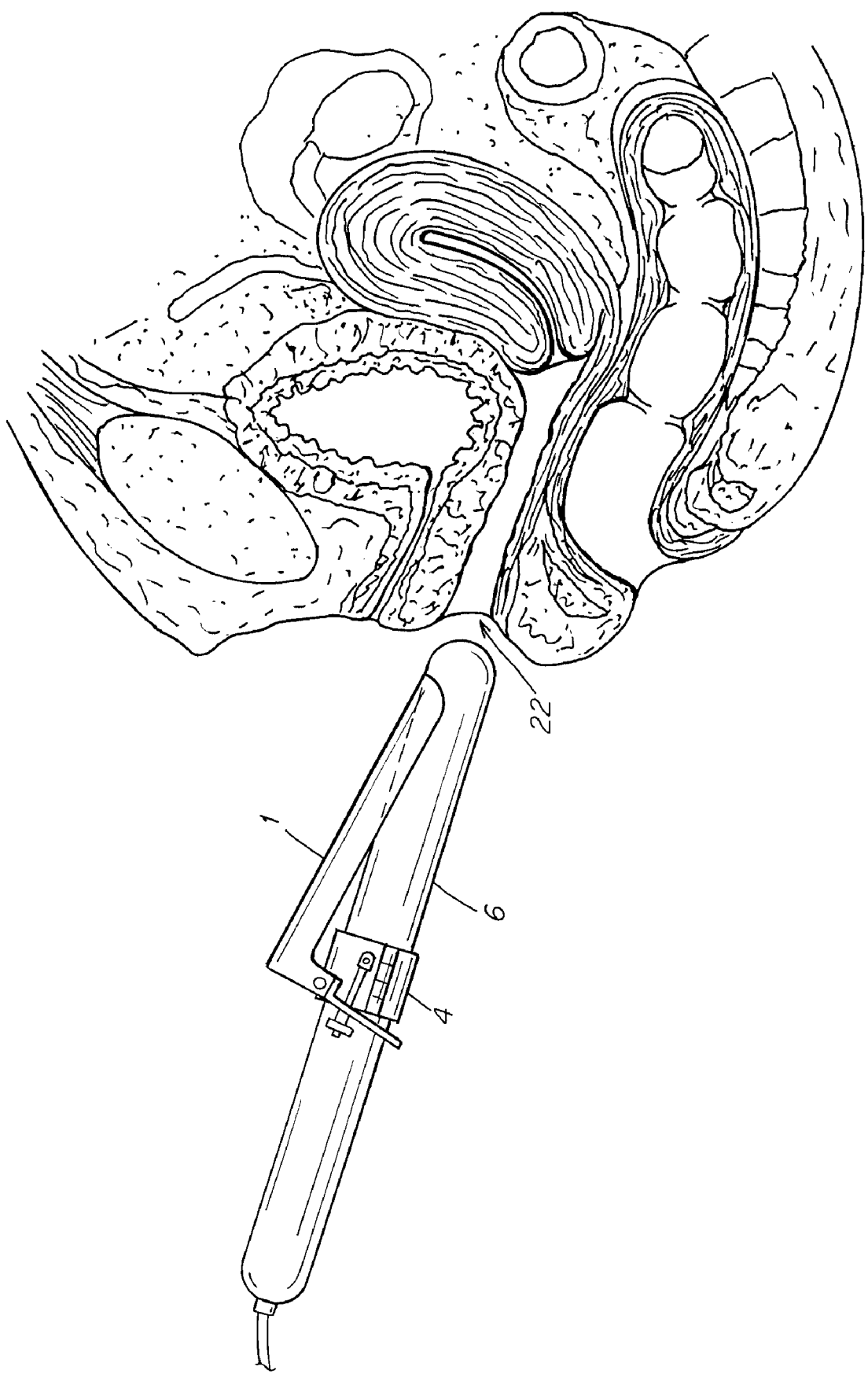
FIG. 6 is a view of the speculum with the blade in a closed position being inserted into the vagina
Figure 7:
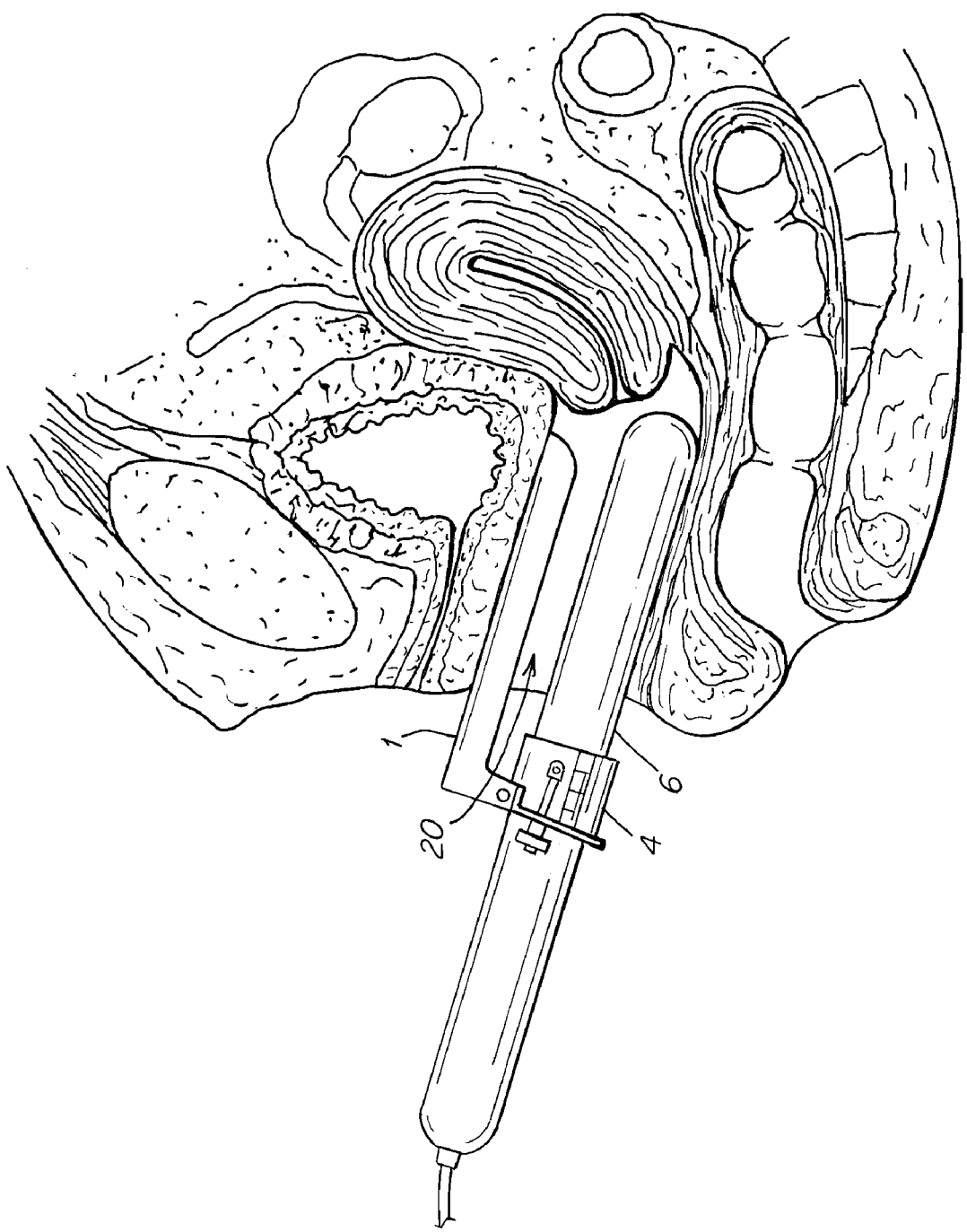
FIG. 7 is a view of the speculum in the vagina with the blade in an open position.

As shown in FIG. 2, the speculum has a lever 7 coupled to collar 4 and to elongated blade 1 for manual actuation to pivot blade 1 relative to ultrasound probe 6 so that blade 1 and ultrasound probe 6 serve as the blades of the speculum. When force is applied to lever 7 (e.g., by pressing lever 7), blade 1 pivots away from ultrasound probe 6. Blade 7 is shown pivoted in an open position away from ultrasound probe 6 in the full lines and is shown in the closed position in the dashed lines. Lever 7 allows blade 1 and ultrasound probe 6 to be moved between an open position and a closed position depending on the situation, e.g., in a closed position for insertion into a vagina (as shown in FIG. 6) and in an open position after insertion into the vagina for use during a gynecological procedure or examination (as shown in FIG. 7).

Blade 1 can serve as the anterior blade of the speculum and ultrasound probe 6 can serve as the posterior blade of the speculum. In this embodiment, when force is applied to lever 7, blade 1 pushes the vaginal mucosa in an anterior direction and ultrasound probe 6 pushes the vaginal mucosa in a posterior direction. Once the vaginal mucosa have been pushed aside, visualization of the cervix is possible.

The speculum can also include a lock 8 for maintaining the position of blade 1 relative to ultrasound probe 6. In one embodiment, lock 8 has a nut 12 and a threaded rod 11 that extends through an opening in lever 7. When blade 1 is in a desired position, nut 12 can be tightened along rod 11 so that lever 7 does not allow blade 1 to pivot downwardly toward ultrasound probe 6. This lock allows the blade and ultrasound probe that serve as the blades of the speculum to be maintained in a desired position. Other suitable locks for maintaining the position of the blade relative the ultrasound probe could be used, such as a lock where teeth are pulled passed a lip for catching teeth disposed on the lever. When the desired position of the blade relative to the ultrasound probe is achieved, the tooth corresponding to that position is caught on the lip and maintains the position of the blade relative to the ultrasound probe.

Figure 4:
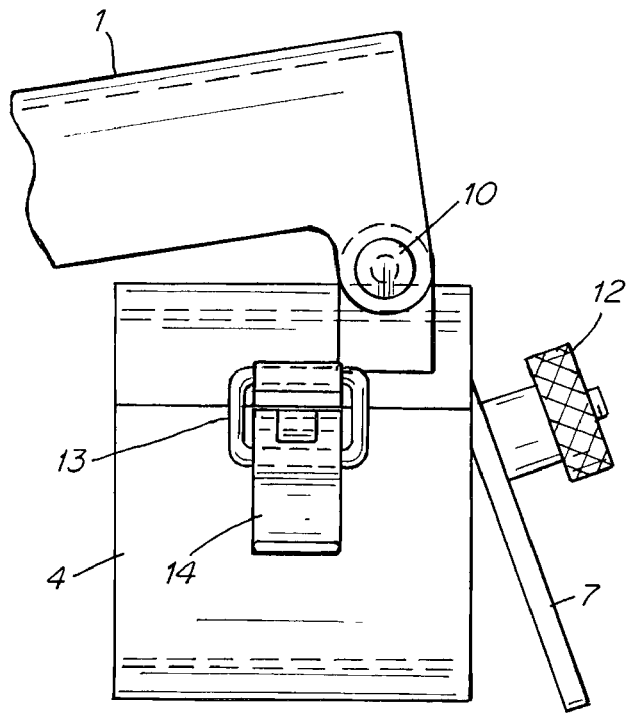
FIG. 4 is a partial side view of a portion of the speculum.
Figure 5:
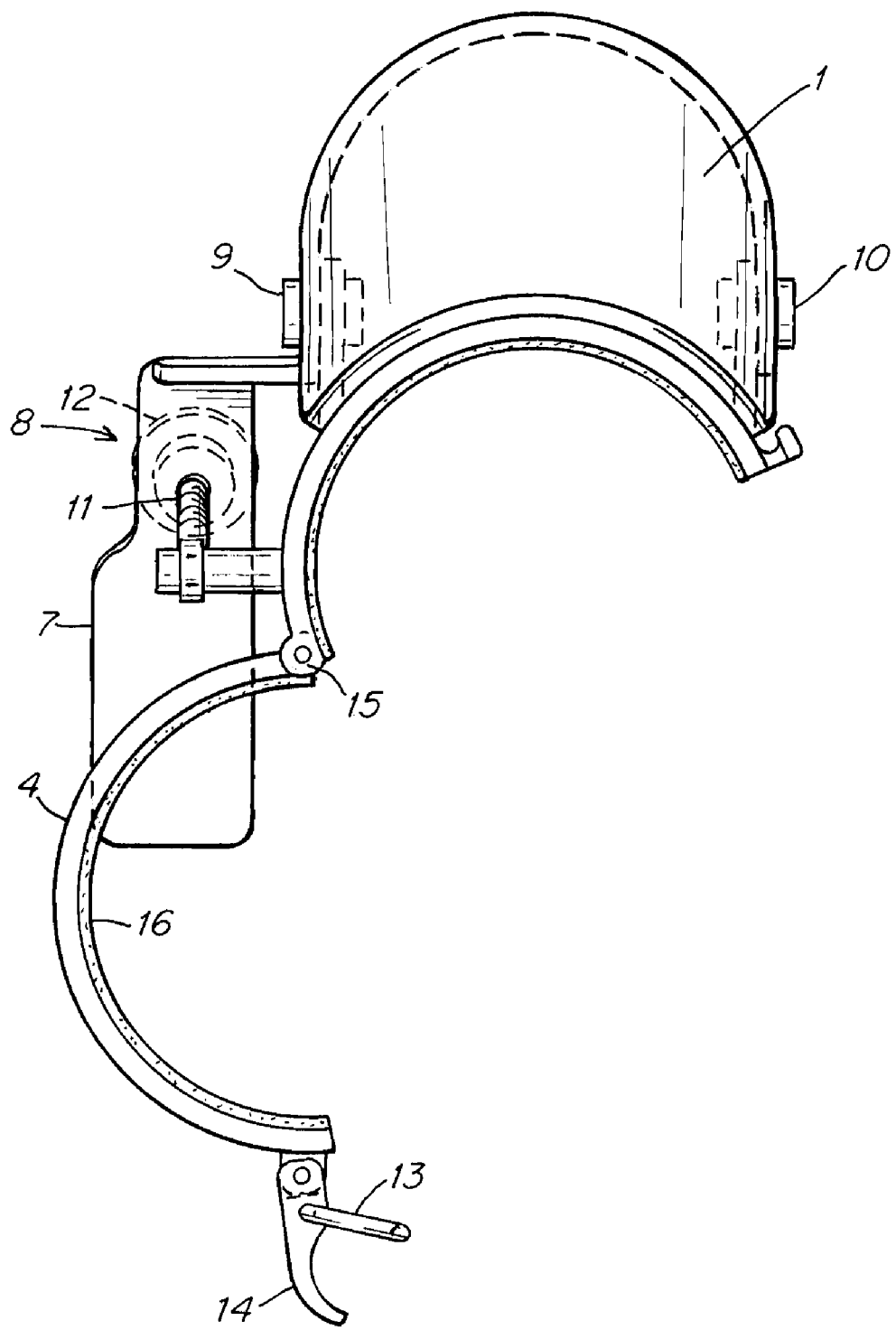
FIG. 5 is a distal end view of the speculum with a collar opened.

FIGS. 3-5 show an embodiment of a connector in more detail. The connector has a collar 4 that includes a hinge 15 that allows the collar to open and receive an ultrasound probe. Once collar 4 is disposed around an ultrasound probe, a latch 13 is connected and tightened by lever 14 to securely hold the ultrasound probe. Although not shown, collar 4 can have multiple connection points for the latch so that the collar can receive and hold ultrasound probes of different diameters. Collar 4 can include any suitable means for receiving and securely holding an ultrasound probe. Other suitable means for allowing the collar to open and receive an ultrasound probe can be used, such as where the collar has teeth that are fed through a lip for catching and holding the teeth. Once an ultrasound probe is placed within the collar, the teeth are pulled passed the lip until the collar securely holds the ultrasound probe. This arrangement allows the device to be used with a variety of available probes because different probes can have different diameters.

The collar can have a variable size so it can hold ultrasound probes of different diameters. It is also not necessary that the collar completely surround the ultrasound probe. Rather, the collar need only be able to securely hold the ultrasound probe. The collar can also include a suitable material at its inner diameter to create an annular layer 16 for helping to grip and hold an ultrasound blade in place relative to the blade. The material can include rubber, plastic, or silicone, and is desirably a compressible material that provides a good grip. FIG. 3 also demonstrates the viewing area 20 through which the practitioner can view the cervix.

As shown in FIG. 3, collar 4 is disposed around ultrasound probe 6. In certain embodiments, the speculum is further combined with an ultrasound probe. In some embodiments, the blades of the speculum consists essentially of the blade and the ultrasound probe.

Although the speculum can be used with many different ultrasound probes having different diameters, the speculum can also be designed for use with a specific probe. In such a case, the collar could be sized and configured to hold a specific type probe without being adjustable, and could have component designed to mate with corresponding components of the probe to make a good connection. Similarly, a probe can be constructed to fit with the collar. Such a probe could, for example, have a groove designed for the collar to fit around. In this case, the collar might not need the same flexibility to adapt to devices. The speculum can also be built to be used multiple times or to be used one time (i.e., it can be disposable).

FIGS. 6 and 7 show a speculum with blade 1 and probe 6 prior to insertion into a vagina 20 (FIG. 6), and with blade 1 and probe 6 spaced apart when in vagina 20 (FIG. 7).

The speculum can be used to perform a gynecological procedure on a patient. In this method, a speculum of this disclosure as described above is inserted into the patient's vagina. Power is secured to the ultrasound probe either before or after the speculum is inserted into the patient's vagina. After the speculum is inserted into the vagina, images provided from the ultrasound probe can be viewed on any suitable ultrasonic viewing equipment.

Once the speculum is positioned in the vagina, the ultrasound probe is positioned proximate to the posterior fornix. This positioning allows transcervical procedures to be performed with direct ultrasound guidance and superior visualization of the uterus, even if the uterus is retroverted. After the speculum is inserted into the vagina and the lever has been pressed so that the vaginal mucosa have been separated, the cervix is exposed, thereby allowing a clinician to directly visualize the cervix, to pass instruments through the opening and into the uterus, as well as being able to view images supplied by the ultrasound probe to suitable ultrasound viewing equipment.

The speculum of this disclosure is useful in any transcervical procedure and the methods of this disclosure can be combined with any transcervical procedure. Such procedures include, but are not limited to, IVF, IUD insertion or removal, saline infusion sonography, and endometrial biopsy. The speculum of this disclosure is also useful for cervical dilation, particularly when the cervix is stenosed.

Those skilled in the art will recognize, or be able to ascertain, using no more than routine experimentation, numerous equivalents to the specific embodiments described specifically in this disclosure. Such equivalents are intended to be encompassed in the scope of the following claims.

What is claimed:

1. A speculum for use with a generally cylindrical elongated ultrasound probe, comprising:
   one and only one blade having a proximal end and a distal end and sized and shaped to form a blade of a vaginal speculum;
   a collar pivotally cooperating with the proximal end of the blade and having an opening for receiving and securely holding the ultrasound probe; and
   a lever cooperating with the collar and the blade for pivoting the blade relative to the ultrasound probe so that the blade and the ultrasound probe serve as first and second blades of the speculum.

2. The speculum of claim 1, wherein the collar is disposed around the ultrasound probe.

3. The speculum of claim 2, wherein the collar is configured to hold ultrasound probes having different diameters.

4. The speculum of claim 1, wherein the collar includes one of rubber, plastic, and silicone at an inside diameter.

5. The speculum of claim 1, further comprising a lock for maintaining the position of the blade relative to the collar.

6. The speculum of claim 1, wherein the blade serves as the anterior blade and the ultrasound probe serves as the posterior blade.

7. A speculum for use with a generally cylindrical elongated ultrasound probe, comprising:
   one and only one blade having a proximal end and a distal end and sized and shaped to form a blade of a vaginal speculum;
   a generally cylindrical elongated ultrasound probe having a proximal end and a distal end and at least one transducer proximate to the distal end;
   a collar pivotally cooperating with the proximal end of the blade and having an opening for receiving and securely holding the ultrasound probe; and
   wherein a first and second blade of the speculum consist essentially of the blade and the ultrasound probe.

8. The speculum of claim 7, wherein the blade includes one of plastic and metal.

9. The speculum of claim 7, further comprising
a lever cooperating with the collar and the blade for pivoting the blade relative to the ultrasound probe so that the blade and the ultrasound probe serve as first and second blades of the speculum.

10. The speculum of claim 9, wherein the collar includes one of rubber, plastic, and silicone at an inside diameter.

11. The speculum of claim 9, wherein the collar is configured to hold ultrasound probes having different diameters.

12. The speculum of claim 7, further comprising a lock for maintaining the position of the blade relative to the ultrasound probe.

13. The speculum of claim 7, wherein the blade serves as an anterior blade and the ultrasound probe serves as a posterior blade.

14. A method of performing a gynecological procedure on a patient, comprising:
inserting the speculum of claim 7 into a patient's vagina; and
generating and viewing images supplied by the ultrasound probe.

15. The method of claim 14, further comprising performing in vitro fertilization.

16. The method of claim 14, further comprising inserting or removing an intrauterine device.

17. The method of claim 14, further comprising performing an endometrial biopsy.

18. The method of claim 14, wherein the speculum is positioned so that the probe functions as the posterior blade.

\* \* \* \* \*